United States Patent [19]

Prechter et al.

[11] Patent Number: 5,039,057
[45] Date of Patent: Aug. 13, 1991

[54] ROLLER-SUPPORTED, MODULAR, ISOCENTRIC GENTRY AND METHOD OF ASSEMBLY

[75] Inventors: Rudolf E. Prechter, Cranbury; Benjamin A. Prichard, Jr., East Windsor, both of N.J.

[73] Assignee: Loma Linda University Medical Center, Loma Linda, Calif.

[21] Appl. No.: 509,590

[22] Filed: Apr. 12, 1990

Related U.S. Application Data

[62] Division of Ser. No. 178,471, Apr. 7, 1988, Pat. No. 4,917,344.

[51] Int. Cl.$^5$ .............................................. G01N 21/00
[52] U.S. Cl. ..................... 248/664; 250/492.3
[58] Field of Search ............... 250/492.3, 491.1; 248/664

[56] References Cited

FOREIGN PATENT DOCUMENTS

1194400 8/1986 Japan ............................... 250/492.3

Primary Examiner—Alvin C. Chin-Shue

[57] ABSTRACT

An earthquake resistant, roller-supported, modular, isocentric gantry for supporting and rotating a radiation beam transport and delivery system on an axis of rotation around a stationary patient so as to precisely deliver a treatment beam to a predetermined target isocenter within the patient from several different angles during patient treatment. The gantry is formed of three primary building blocks: a conical inner support structure, an outer segmented, modular truss structure and a ladder truss which may be assembled in the field to form an isocentric gantry.

2 Claims, 8 Drawing Sheets

ROLLER-SUPPORTED, MODULAR, ISOCENTRIC GENTRY AND METHOD OF ASSEMBLY

This is a divisional of co-pending application Ser. No. 07/178,471, filed on Apr. 7, 1988, now U.S. Pat. No. 4,917,344, issued on Apr. 17, 1990.

BACKGROUND

The present invention relates to radiation beam therapy systems and more particularly to an improved gantry for use in such systems to support and rotate a radiation beam transport and delivery system around a stationary patient so as to precisely deliver a treatment beam to a predetermined target isocenter within the patient from several different angles during patient treatment. Preferably, the gantry is earthquake resistant, roller-supported for turning on its axis of rotation over a range equal to or greater than plus or minus 185 degrees from a home position and modular in construction for relatively inexpensive construction and assembly within existing structures or structure under construction.

U.S. patent application Ser. No. 07/163,611, filed Mar. 3, 1988. describes and illustrates a radiation beam therapy system including several different treatment stations each including a gantry for supporting and rotating a radiation beam transport and delivery system on an axis of rotation around a stationary patient to deliver a treatment beam to a predetermined target isocenter within the patient from several different angles during patient treatment. It is stated that the gantry structure may conform to the gantry described in a publication of the Harvard Cyclotron Laboratory entitled "Preliminary Design Study for a Corkscrew Gantry" authored by A. M. Koehler and an application for United States Patent entitled "Beam Redirecting" filed by Harvard University, Boston, Mass. as Ser. No. 076,868 on July 23, 1987, now U.S. Pat. No. 4,812,688, issued 3/14/89. The publication and patent application describe the gantry as including a single large ring structure carrying heavy counterweights and a portion of a beam delivery system. The ring is supported only by rollers for turning in a vertical plane on a horizontal axis. Such a design is laterally and axially unstable particulary in seismic environments. Because of such instability, even with very careful machining of the ring, the gantry is not capable of reliably meeting a one millimeter concentricity of isocenter specification for a treatment beam delivered by the beam delivery system. More recently, a different gantry design has been proposed by MEDCYC of Lansing, Mich. The MEDCYC design includes two concentric ring structures separated by axially extending brace members which support a heavy cyclotron and an opposing counterweight structure. A beam from the cyclotron is directed at an isocenter located on the axis of rotation of the pair of rings. Due to the weight of the cyclotron and counterweights, the brace members are subject to radial deflection with rotation of the gantry. Such deflection will materially impair the ability of the gantry to consistently meet the isocenter concentricity requirements for radiation beam therapy systems. Furthermore, the MEDCYC design will be subject to undesired instabilities during seismic conditions.

Accordingly, there is a need for a gantry which is able to maintain the desired concentricity of its isocenter during seismic conditions and which is relatively simple in its construction and assembly. The gantry of the present invention satisfies such needs.

SUMMARY OF INVENTION

The present invention provides an earthquake resistant, roller-supported, modular, isocentric gantry for supporting and rotating a radiation beam transport and delivery system around a stationary patient so as to precisely deliver a treatment beam from several different angles to a predetermined target isocenter within the patient. To accomplish such goals and to provide a gantry which is sturdy yet simple in construction and relatively easy to assemble, the gantry of the present invention comprises an inner support structure and a segmented truss formed of separate truss modules that are easily assembled into an annular truss circumscribing the inner support structure. The inner support structure comprises vertically extending, parallel and concentric front and rear circular rings separated by axially extending brace members. The front and rear rings are supported by rollers for rotation on a common axis of rotation. The truss is secured to the inner support structure and is assembled by securing a first truss module to the inner support structure, rotating the inner support structure, securing a second truss module to the first and to the inner support structure and so forth until the annular truss is completed and circumscribes the inner support structure to provide structural strength against deflection of the gantry upon the occurrence of a seismic condition. Thus assembled, the rear ring carries means for supporting an entry element of the beam transport and delivery system for turning on the axis of rotation while the front ring and/or a brace member between tha front and rear rings carries means for supporting an exit element e.g. a nozzle, of the beam delivery system to precisely deliver the treatment beam at the target isocenter on the axis of rotation independent of the rotational position of the gantry. Because the inner support structure is laterally and axially stable on the axis of rotation and is free from deflections by virtue of the truss, the mounting of the exit element of the beam delivery system on the front ring and/or a brace member between the front and rear rings insures that the treatment beam is precisely directed at the target isocenter independent of seismic conditions. Not only does the truss provide structural strength for the gantry, together with a connecting support member between the rear ring and the truss e.g. a truss ladder, it also provides support for intermediate elements of the beam transport and delivery system such that the intermediate elements turn with the gantry around the axis of rotation in response to operation of a motor drive coupled to certain of the support rollers for the inner support structure.

BRIEF DESCRIPTION OF DRAWINGS

FIG. 1a is a front view of the isocentric gantry of the present invention carrying a beam transport and delivery system while FIG. 1b is a sectional side view of the gantry along the section line 1b—1b included in FIG. 1a.

FIG. 2a is a side view of the inner cone-shaped support structure of the gantry while

FIG. 4a is a front view of the segmented truss which circumscribes the inner support structure while FIG. 4b is a sectional side view of the truss along the section line 4b—4b in the front view.

FIG. 5a is a side view of the truss ladder connecting the rear ring and the truss while

FIG. 6a is a front view of the isocentric gantry while

FIG. 7a is a front view of the roller support for the front ring of the inner support structure while FIG. 7b is a sectional view along the section line 7b—7b in FIG. 7a.

FIG. 8a is an enlarged quarter section of the roller support shown in FIG. 7a.

FIG. 8b is a sectional view along the section line 8b—8b in FIG. 8a.

FIG. 9a is a front view of the roller support system for the rear ring of the inner support structure while FIG. 9b is a section view of the roller support along the section line 9b—9b in FIG. 9a.

DETAILED DESCRIPTION OF INVENTION

Figure 1A:
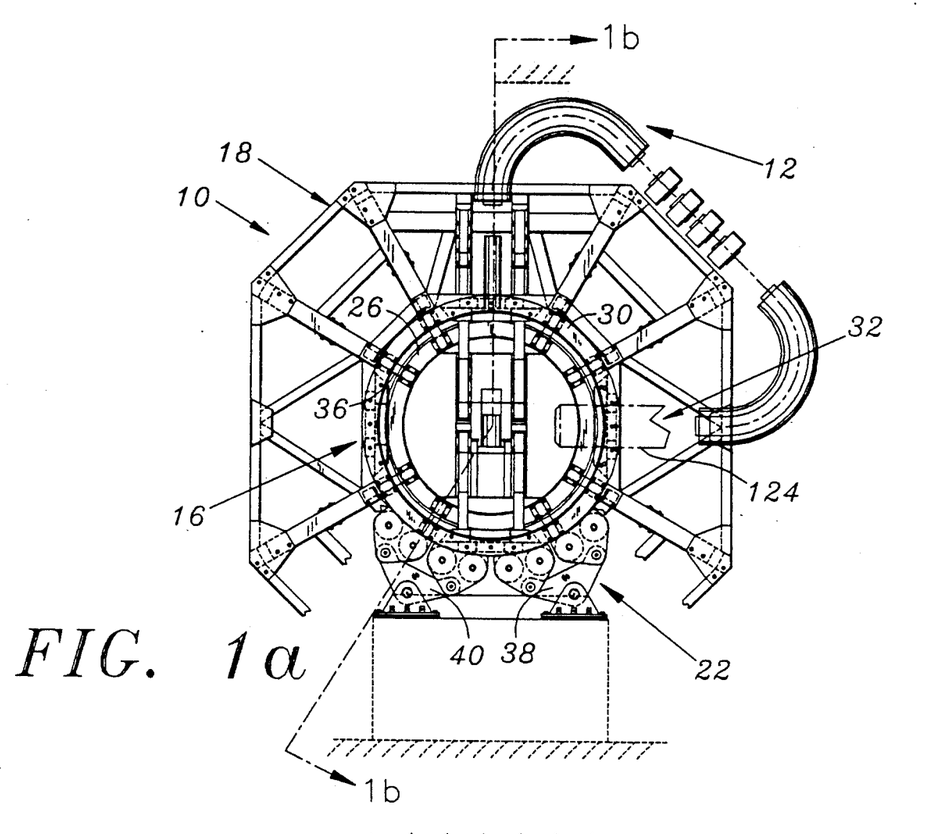
Figure 1B:
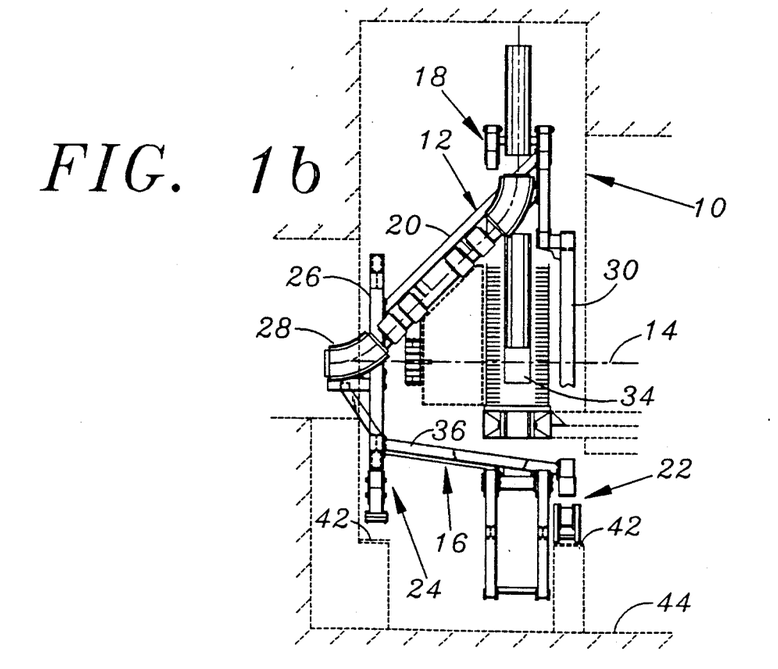

FIGS. 1a and b illustrate a gantry 10 supporting a radiation beam transport and delivery system 12 for rotation on an axis of rotation 14. The gantry is about thirty six feet in diameter, twelve feet in length, weighs about 150,000 to 200,000 pounds, and when supported by rollers as hereinafter described, can be rotated at least plus and minus 185 degrees in a vertical plane by means of motor and gear reduction drives controlled by local and remote computer controls.

Figure 3:
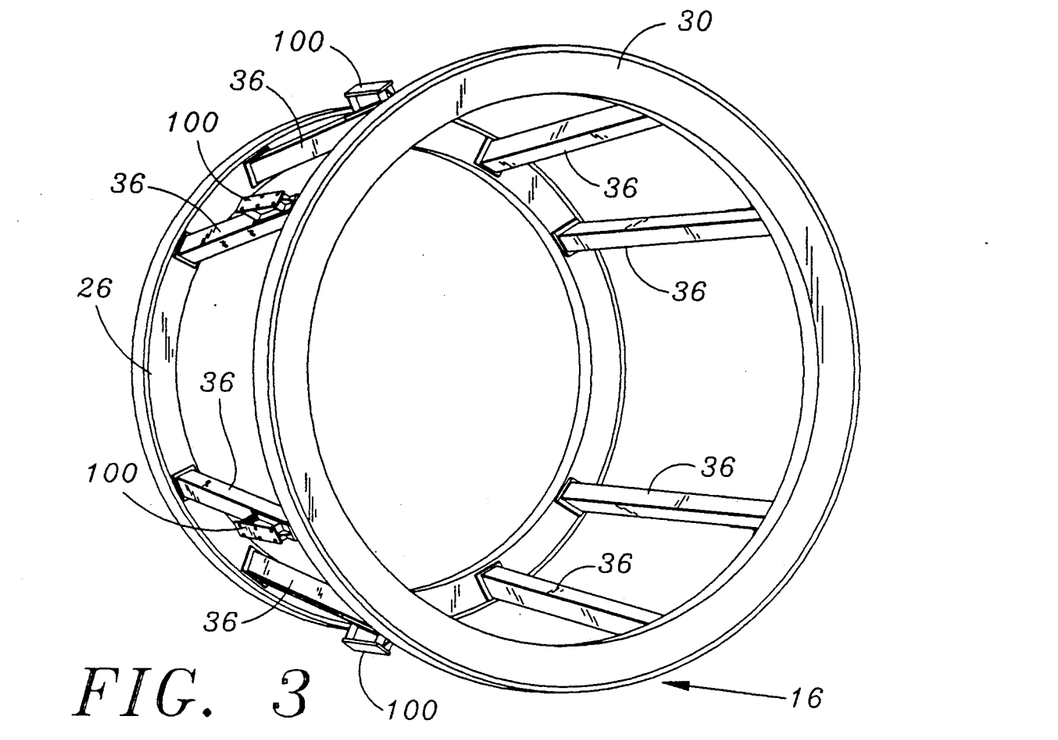
FIG. 3 is a perspective view of the cone-shaped inner support structure.
Figures 4A, 4B:
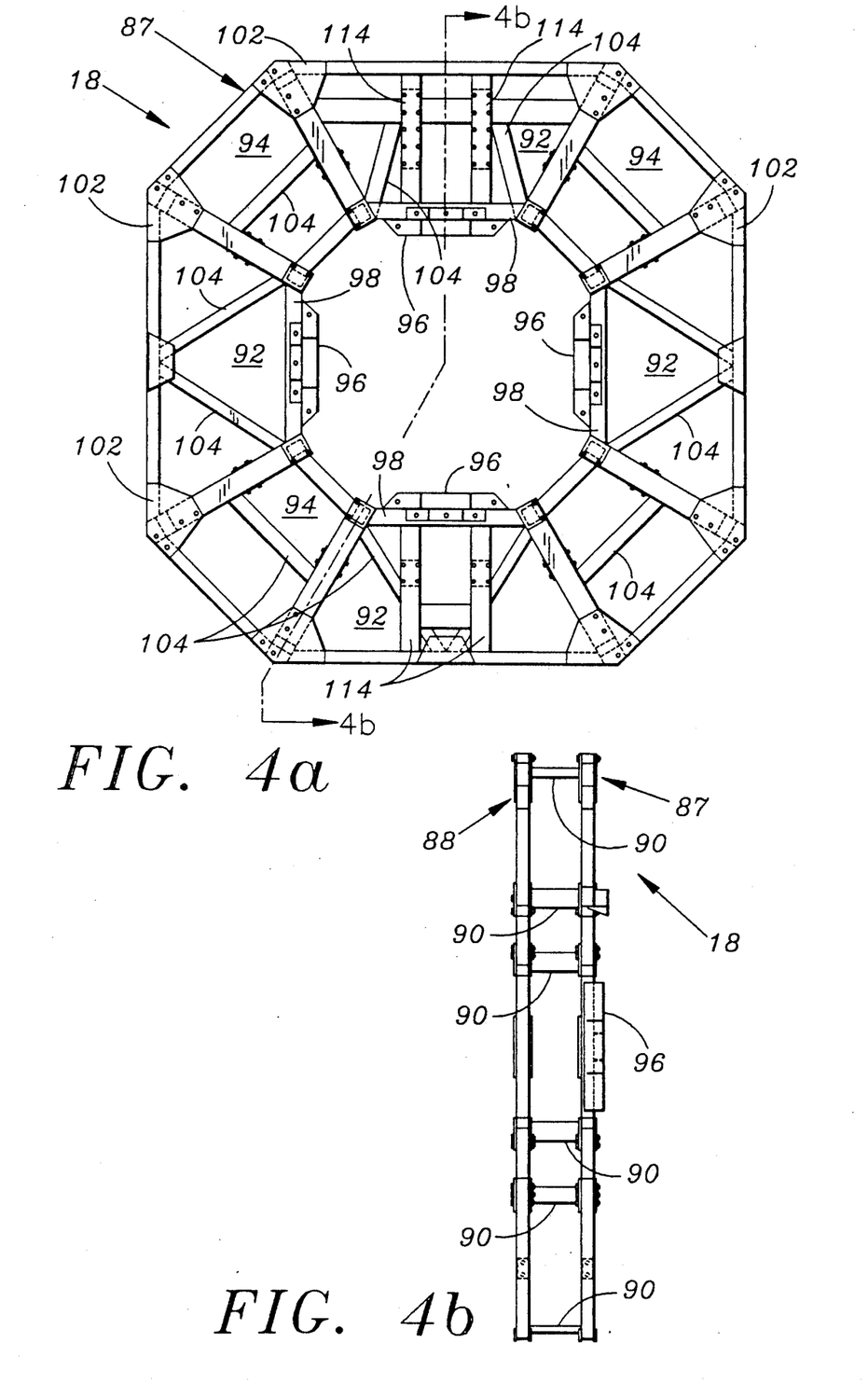
Figure 5A:
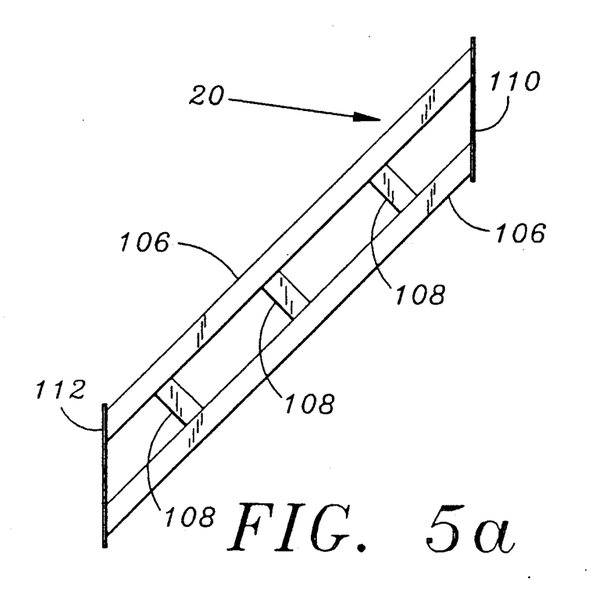
Figure 5B:
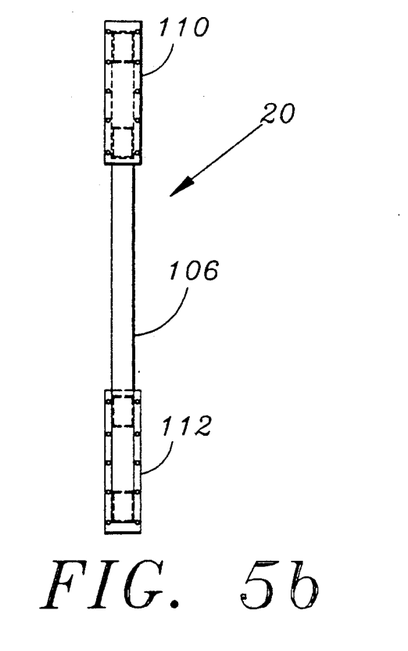
FIG. 5b is a front view of the truss ladder.
Figure 6A:
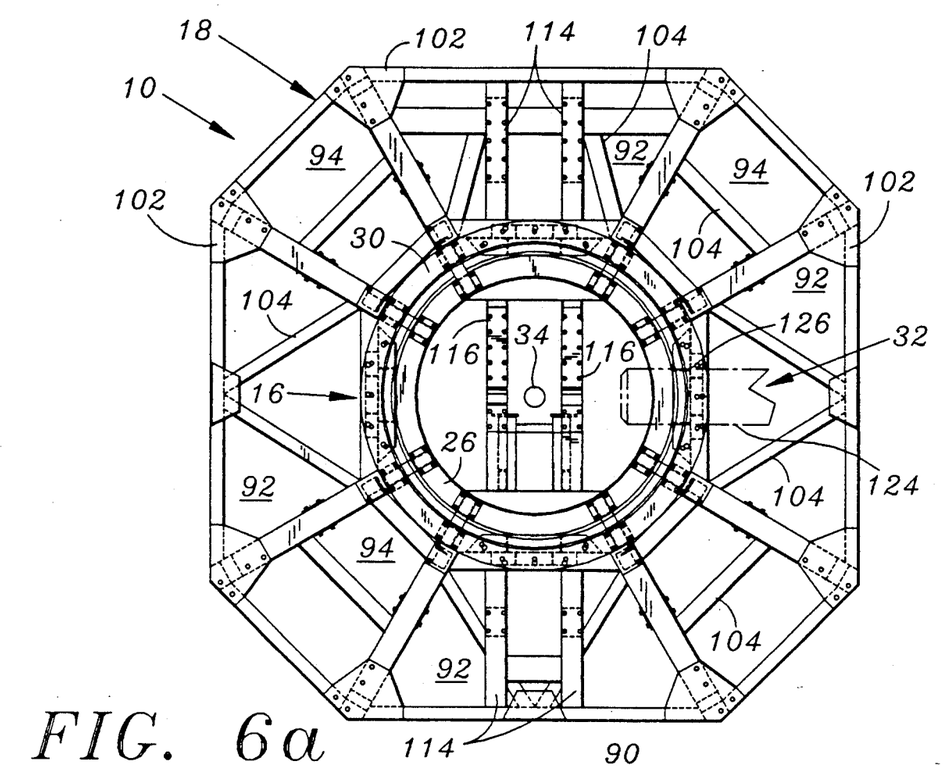
Figure 6B:
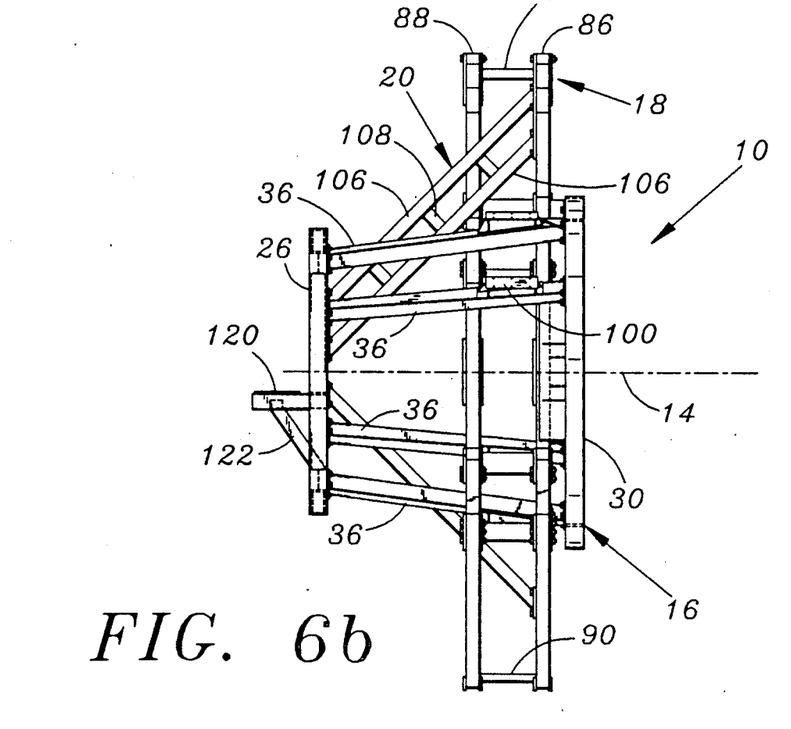
FIG. 6b is a side view of the gantry.
Figures 7A, 7B:
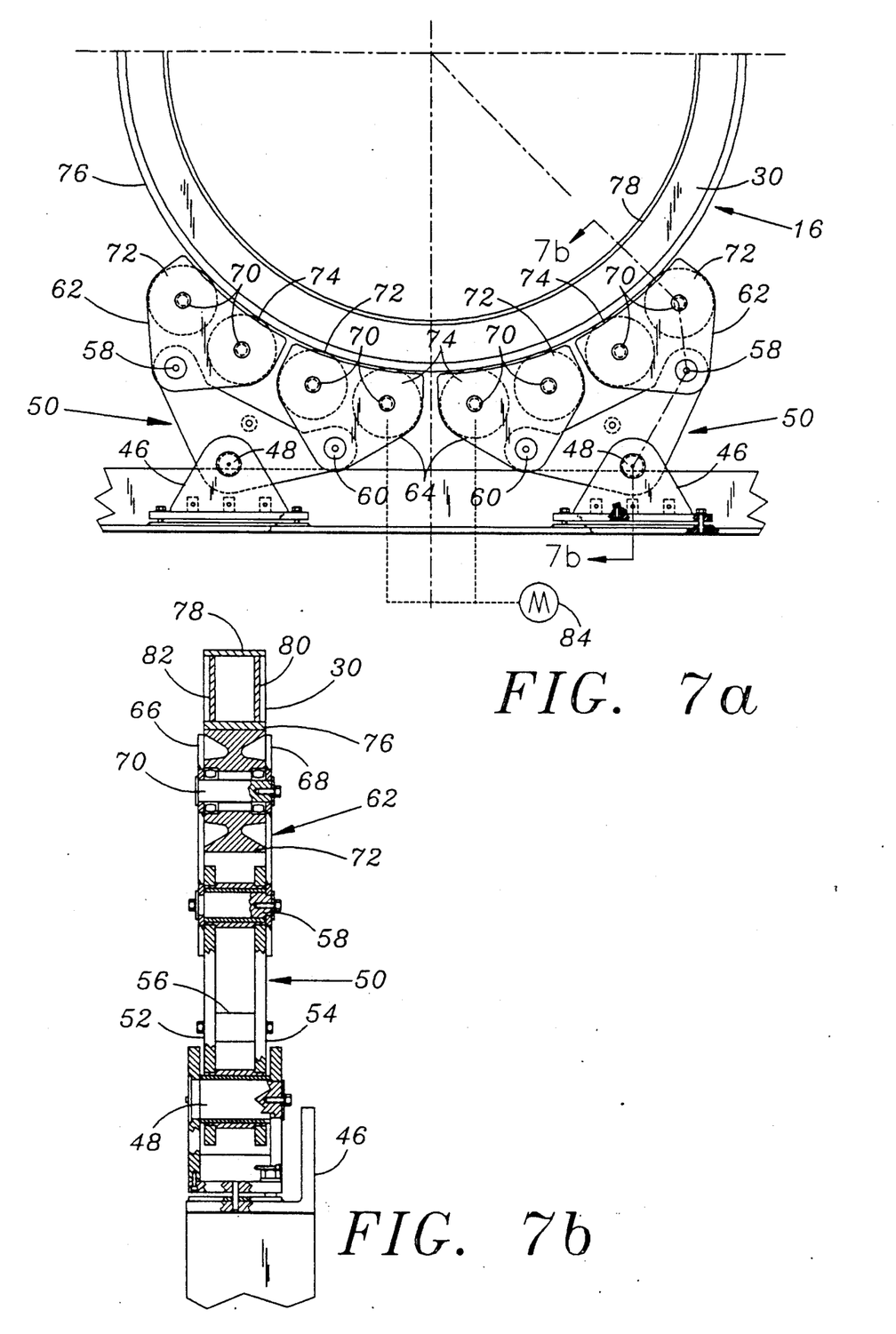
Figure 8A:
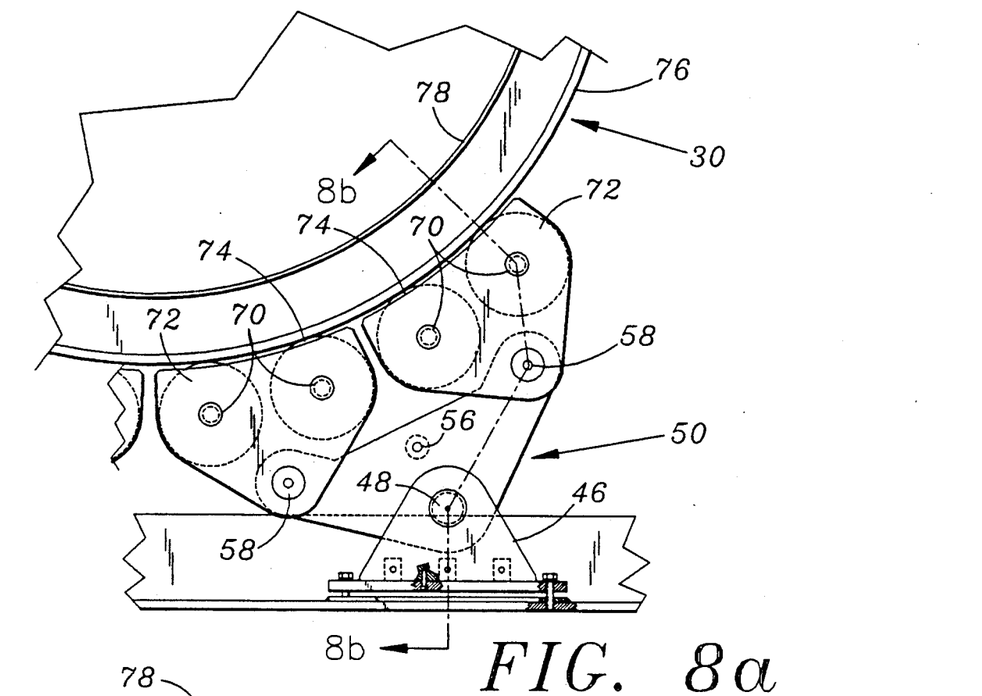
Figure 8B:
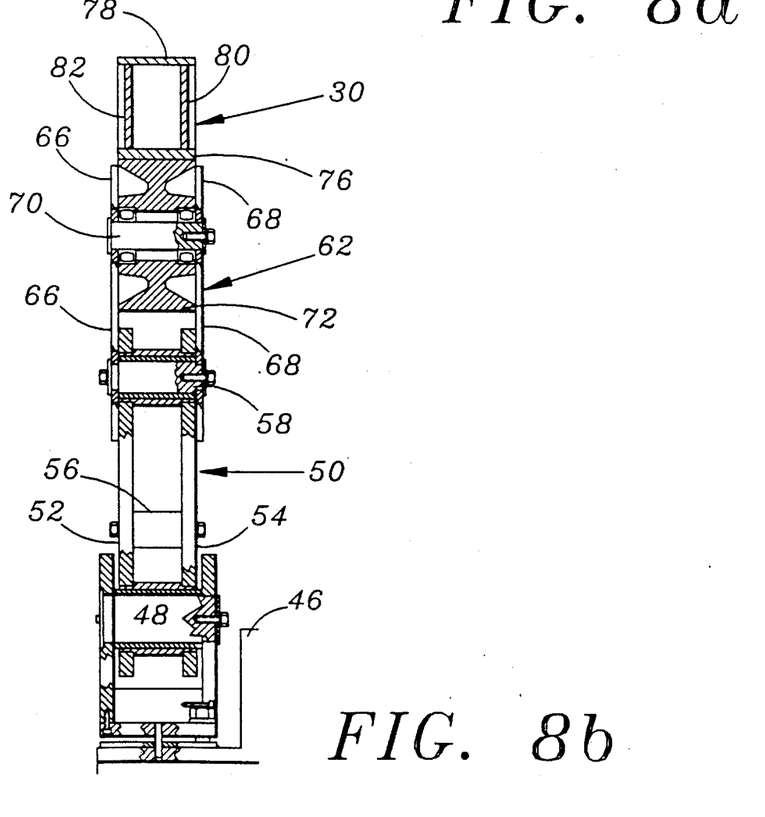

The gantry 10 consists of three primary building blocks: a conical inner support structure 16 (FIGS. 2a and b and 3), an outer, segmented, modular truss structure 18 (FIGS. 4a and b), and a ladder truss 20 (FIGS. 5a and b). The three primary structures are assembled in the field to form the basic isocentric gantry 10 shown in FIGS. 6a and b.

As shown in FIGS. 1a and b, the conical inner support structure 16 is laterally supported by axially separated front and rear roller assemblies 22 and 24 for rotation on the axis 14 with the outer segmented modular truss 18 secured to and circumscribing the conical structure 16. A concentric rear ring 26 of the conical inner structure supports an entry element 28, e.g. a bending magnet, of the beam transport and delivery system 12 for rotation on the axis of rotation 14 while a concentric front ring 30 of the conical structure 16 carries means supporting an exit element, e.g. a nozzle 32 of the beam transport and delivery system, for turning on the axis 14 with the exit port of the nozzle directed at a predetermined target isocenter 34 on the axis 14. The truss 18 and the ladder truss 20 connected between the rear ring 26 and the truss support intermediate elements of the beam transport and delivery system 12 for turning on the axis 14. Thus supported, radiation beams entering the bending magnet 28 are transported and directed by the intermediate elements to exit from the nozzle 32 for precise delivery to the target isocenter 34 independent of the rotational position of the gantry. By virtue of the lateral and axial strength provided by the truss 18 and ladder truss 20, such precise delivery of the beam to the target isocenter is maintained even during seismic conditions.

Figure 2A:
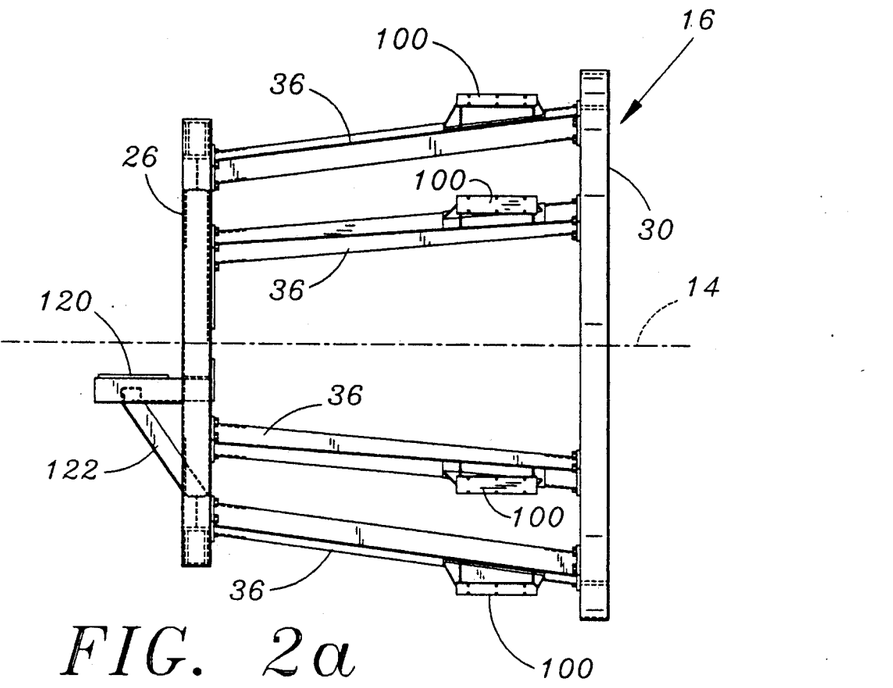
Figure 2B:
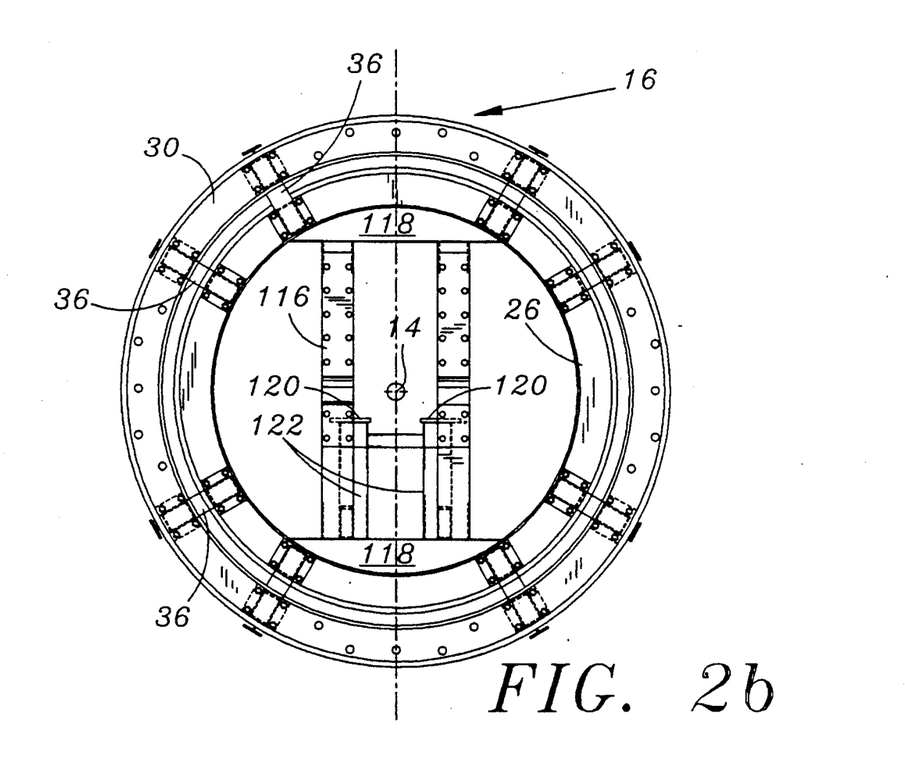
FIG. 2b is a front view of the cone-shaped structure.

More particularly, and as illustrated most clearly in FIGS. 2a and b and 3, in the conical inner support structure 16, the front and rear rings 30 and 26 are relatively large and small respectively. The rings ar axially separated and fixedly secured by a plurality of axially extending brace members 36 which maintain a parallel concentric relationship between the rings.

The front and rear roller assemblies 22 and 24 supporting the conical inner structure for rotation on the axis 14 are most clearly shown in FIGS. 1a and b, 7a and b, 8a and b and 9a and b. As there depicted, the front roller assembly 22 includes two identical roller subassemblies 38 and 40 mounted on a base structure 42 rising above a floor 44 and on the right and left side respectively of the axis 14. The two identical subassemblies each include an L-shaped mounting bracket 46 and associated pivot assembly 48. The pivot assembly 48 supports a V-shaped support arm assembly 50 consisting of vertically extending front and rear plates 52 and 54 separated by a cross brace 56. The support assembly 50 in turn, supports by horizontal pivots 58 and 60, right and left V-shaped support plate assemblies 62 and 64 each formed by front and rear parallel plates 66 and 68 carrying on horizontal axles 70 two pairs of cylindrical rollers 72 and 74. The rollers 72 and 74 are constructed to make rolling contact with and provide support for an outermost rim 76 of the ring 30 to support the ring 30 for rotation on the axis 14.

In this regard, in the assembly of the gantry 10, the mounting brackets 46 are first secured to the base structure 42 equally spaced from and on the right and left side of a vertical plane including the axis 14 with the pivots 48, 58 and 60 and the axles 70 all lying in horizontal planes parallel to a horizontal plane including the axis. The front ring 30 is then lowered onto the roller assembly 22 with the outer rim 76 riding on the rollers 72 and 74 of each roller pair. Incidently, as shown most clearly in cross-section in FIGS. 8 and 9, the rings 26 and 30 are of hollow light-weight yet sturdy and rigid construction each comprising an outer rim 76 and a concentric inner rim 78 extending latterly beyond vertically extending sidewalls 80 and 82.

Figure 9A:
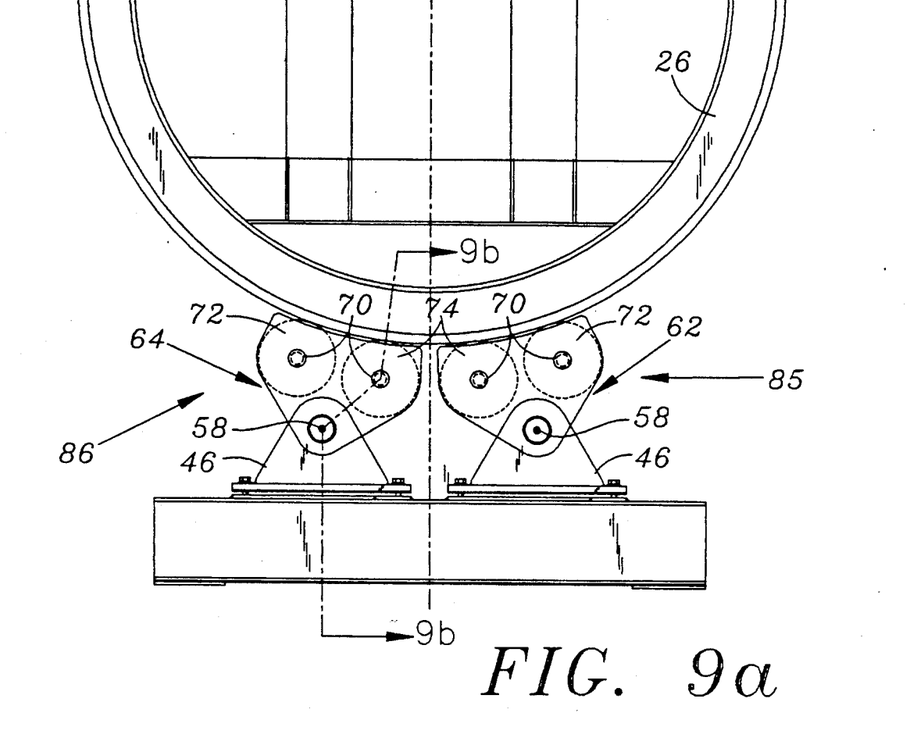
Figure 9B:
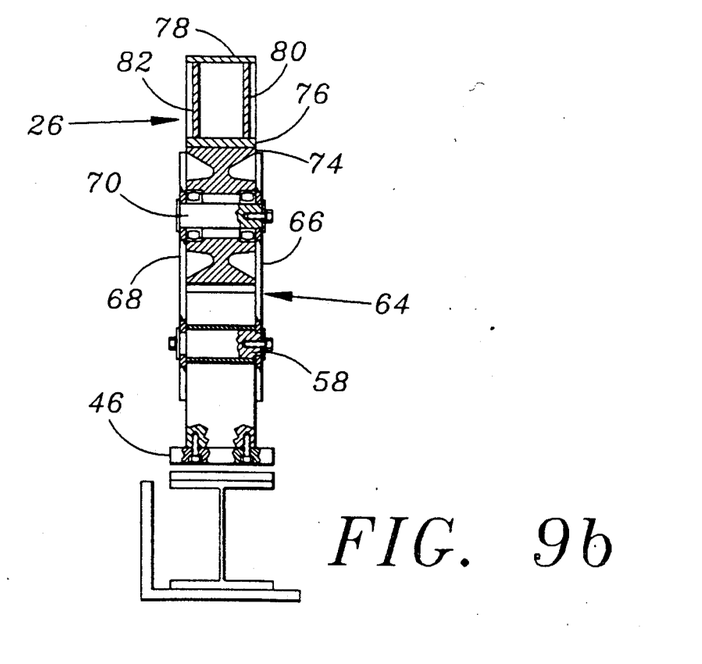

As shown most clearly in FIGS. 9a and b, the rear ring 26 of the conical inner structure is supported by roller subassemblies 84 and 86 which are nearly identical to the subassemblies 38 and 40. Accordingly, identical numbers will be applied to identical components of the subassemblies 85,86 and 38,40 and a description thereof will not be repeated. Of course in the assembly of the gantry, the roller subassemblies 85 and 86 are mounted on the base structure 42 above the floor 44 before the positioning of the conical inner structure 16 so that as the front ring is lowered onto the roller subassemblies 38 and 40 on opposite sides of the vertical plane including the axis 14, the rear ring 26 is lowered onto the roller subassemblies 85 and 86 equally spaced on the right and left of the same vertical plane. Thus positioned, the axis 14 lies in a horizontal plane and the concentric rings 26 and 30 are laterally secured by the roller assemblies 22 and 24 for rotation in vertical front and rear planes on the axis in response to operation of a motor drive 84. The motor drive is depicted diagramically in FIGS. 7a and b as being coupled to rollers of the subassemblies 38 and 40. Because of the rigid connection between the front and rear rings 30 and 26 by the brace members 36, rotational drive from the motor drive 84 to the front ring 30 is translated to the rear ring 26 to produce a simultaneous turning of the rings in response to the drive motor.

Turning simultaneously with the conical inner structure 16 is the outer segmented modular truss 18. The structure of the truss and its connection to the conical inner structure are most clearly shown in FIGS. 4a and b and 6a and b. As illustrated, the truss 18 includes two similar annular truss portions 87 and 88 separated and secured togther by horizontal brace members 90. Each truss portion consists of four relatively large and four relatively small trapezodially shaped truss modules 92 and 94 respectively, connected in the form of an octagon. The modules 92 and 94 are intended to be connected in sequence to each other and to the conical inner structure 16 after the conical inner structure is mounted in place as previously described. Thus for example, after the conical structure is in place, a first one of the large modules 92 of the truss portion 87 is secured to the front ring 30 as by bolts connected through a mounting plate 96 secured to the short leg 98 of the tradezoid comprising the module and extending into a back side of the ring 30 or a bracket extending therefrom. Then, a similar first one of the large modules 92 of the truss portion 88 is secured to the previously described large module 92 of the truss portion 86 as by connecting one of the horizontal brace members 90 to and between the modules at a junction of the truss elements defining the innermost sides of the tradezoids and by bolting the brace member to a radially extending pad 100 connected to and carried by one of the brace members 36 of the conical inner structure 16. The conical inner structure is then rotated a few degrees and the foregoing process repeated for relatively small truss modules 94 in the truss portions 87 and 88. For example, a small truss module 94 of the truss portion 86 may be positioned next to the previously secured in place large module 92 of the truss portion 87 and bolted thereto. Then, a small module 94 of the truss portion 88 is secured to the small module 94 of the truss portion 87 by connecting horizontal brace members 90 between the modules 94 and by bolting the innermost brace to one of the mounting pads 100 carried by a brace member 36 and to a similar brace for the modules 92. After the large and small modules are secured in place, a side plate 102 may be secured to an outer corner of the adjacent large and small modules 92 and 94. Then, the conical inner structure 16 is again rotated a few degrees and the process is repeated for two large modules 92 of the truss portions 86 and 88 and then for two small modules 94 of the truss portions 86 and 88 and so on until the truss 18 is completed and is of octagon form with brace members 90 secured to the brace members 36 of the conical inner structure 16 and with alternate large and small trapezodial truss modules 92 and 94 secured together. As illustrated in FIGS. 4a and b and 6a and b, additional cross braces 104 may be added to the finished truss to insure the desired regidity and strength of the truss and conical inner structure combination against any anticipated seismic condition.

Further, after the truss 18 is secured to the conical inner structure 16, the truss ladder 20 is connected between the rear ring 26 of the inner structure 16 and the truss 18 to provide additional axial strength and means for carrying intermediate elements of the beam transport and delivery system 12. The ladder truss 20 and its connection to the rear ring 26 and the truss 18 are most clearly shown in FIGS. 5 and 6. As illustrated, the ladder truss 20 comprises two vertically aligned, parallel side members 106 and a plurality of connecting cross members or rungs 108 of the ladder. The side members 106 terminate in vertical mounting plates 110 and 112 for connecting the ladder truss to the rear ring and to the truss respectively.

To provide a connection for the truss ladder 20 to the truss, one of the large modules 92 of the truss portion 86 includes two parallel braces 114 extending between and normal to the relatively short and long parallel legs of the tradezoid comprising the module 92. The mounting plate 110 is connected as by bolts to one of the braces 114.

To provide a connection for the truss ladder 20 to the rear ring 26 of the conical inner structure 16, two parallel brace members 116 are secured by mounting plates 118 within the rear ring 26 on opposite sides of the axis 14. The mounting plate 112 of the ladder truss 20 is secured to one of the brace members 116.

To provide support for the bending magnet 28 for rotation on the axis 14, the rear ring 26 carries a support structure most clearly shown in FIGS. 1a and b and 6a and b. As illustrated, the support structure comprises one of the mounting plates 118, two platforms 120, and two inclined braces 122 between the plate and the platforms. The platforms 120 are spaced slightly from the axis 14 so as to support the bending magnet 28 with its axis aligned with the axis 14.

To support the nozzle 32 so that its exit port is directed at the target isocenter 34 on the axis 14, the nozzle may be enclosed in a cylinder 124 and the cylinder secured as by bolts and connecting brackets 126 to one of the brace members 36 of the conical inner structure 16 or directly to the front ring 30. Such a support connection is diagrammatically depicted in FIGS. 1a and b and 6a and b.

Having described a preferred form of the gantry of the present invention and its method of assembly, the inventive features thereof are set forth in the following claims.

We claim:

1. A method of assembling an earthquake resistant gantry for supporting and rotating a radiation beam transport and delivery system so as to deliver a treatment beam to a predetermined target isocenter within a patient, the method comprising the steps of:

mounting an inner support structure including fixedly separated, parallel front and rear concentric circular rings for rotation on an axis or rotation;

connecting a first truss module of an annular segmented truss to extend radially from the inner support structure;

turning the inner support structure on the axis of rotation and connecting a second truss module to the first truss module and to extend radially from the inner support structure;

repeating the turning and truss module connection steps until an annular segmented truss is completed which circumscribes the inner support structure and rotates wherewith on the axis of rotation; and connecting an outwardly inclined member between the rear ring and the truss whereby the rear ring will support an entry element of the beam transport and delivery system for rotation on the axis of rotation, the inclined support member and annular truss will support intermediate elements of the beam transport and delivery system and means carried by the front ring or a brace member between the front and rear rings will support an exit element of the beam transport and delivery system directed at the target isocenter on the axis of rotation to deliver the treatment beam to the target isocenter independent of the rotational position of the gantry.

2. The method of claim 1 wherein the step of mounting the inner support structure for rotation on the axis of rotation includes the steps of;

mounting front and rear pairs of roller assemblies on supports to extend vertically above a floor structure with an axial spacing conforming to the fixed separation of the front and rear rings of the inner support structure and with the rollers of the front and rear pairs laterally spaced on opposite sides of the axis of rotation; and positioning the front and rear rings on the front and rear pairs of roller assemblies respectively to rotate on the axis of rotation with the annular truss extending vertically into a space defined by the roller assembly supports above the floor.

* * * * *